United States Patent [19]

Takahashi et al.

[11] Patent Number: 5,229,422
[45] Date of Patent: Jul. 20, 1993

[54] EXTEMPORANEOUS PREPARATION TYPE KIT OF A PHARMACEUTICAL SUBSTANCE-CONTAINING FAT EMULSION

[75] Inventors: Ken Takahashi; Yuji Makino; Yoshiki Suzuki; Tatsuyuki Naruchi, all of Hino, Japan

[73] Assignee: Teijin Limited, Osaka, Japan

[21] Appl. No.: 715,018

[22] PCT Filed: Sep. 5, 1988

[86] PCT No.: PCT/JP88/00889
§ 371 Date: May 4, 1989
§ 102(e) Date: May 4, 1989

[87] PCT Pub. No.: WO89/02265
PCT Pub. Date: Mar. 23, 1989

Related U.S. Application Data

[63] Continuation of Ser. No. 378,519, May 4, 1989, abandoned.

[30] Foreign Application Priority Data

Sep. 7, 1987 [JP] Japan ............... 62-222130
Sep. 7, 1987 [JP] Japan ............... 62-222131

[51] Int. Cl.⁵ .................... A61K 31/20; A61K 31/13; A61K 31/01
[52] U.S. Cl. ........................ 514/558; 514/669; 514/762; 514/943
[58] Field of Search ............ 514/943, 669, 762, 558

[56] References Cited

U.S. PATENT DOCUMENTS

| | | | |
|---|---|---|---|
| Re. 32,393 | 4/1987 | Wretlind et al. | 514/219 |
| 3,549,752 | 12/1970 | Ercelli et al. | 514/170 |
| 3,833,743 | 9/1974 | Morse et al. | 426/72 |
| 4,259,323 | 3/1981 | Ranucci | 424/679 |
| 4,290,910 | 9/1981 | Harada et al. | 252/312 |
| 4,678,807 | 7/1987 | Cotter et al. | 514/552 |
| 4,784,845 | 11/1988 | Desai et al. | 424/80 |
| 4,816,247 | 3/1989 | Desai et al. | 424/80 |

FOREIGN PATENT DOCUMENTS 2441761 3/1976 Fed. Rep. of Germany .
2112759 6/1972 France .
2300574 10/1976 France .

OTHER PUBLICATIONS

Fortner et al, *Am. J. Hosp. Pharm.*, 32:582-584 (1975).
El-Sayed et al, *Int'l. J. Pharmaceutics*, 13:303-312 (1983).
*Chemical Abstracts*, 101:375 (1984) Huang, L et al.
Physicians Desk Reference (Ed: Carrie. Henwood) pub. by Edward Barnhart (1990) 44th Edition pp. 502-2455.

*Primary Examiner*—Allen J. Robinson
*Assistant Examiner*—Gary E. Hollinden
*Attorney, Agent, or Firm*—Sughrue, Mion, Zinn, Macpeak & Seas

[57] ABSTRACT

An extemporaneous kit of pharmaceutical substance-containing fat emulsion which consists of a fat emulsion and (a) a pharmaceutical substance composition containing pharmaceutical substance and at least one solvent selected from the group consisting of water, liquid polyalkylene glycols, liquid alkylethanolamines, and liquid polyhydric alcohols, or (b) a pharmaceutical substance composition containing pharmaceutical substance and saccharides and/or 30 amino acids as an excipient, and a process for preparation of a pharmaceutical substance-containing fat emulsion therefrom.

10 Claims, No Drawings

EXTEMPORANEOUS PREPARATION TYPE KIT OF A PHARMACEUTICAL SUBSTANCE-CONTAINING FAT EMULSION

This is a Continuation of application Ser. No. 07/378,519, filed May 4, 1989 now abandoned.

FIELD OF THE ART

The present invention relates to an extemporaneous preparation type kit of pharmaceutical substance-containing fat emulsion. More particularly, the present invention relates to an extemporaneous preparation type kit, which is composed of (I) a fat emulsion and (II) a pharmaceutical substance composition and capable of giving a pharmaceutical substance-containing fat emulsion having the pharmaceutical substance embedded in the fat emulsion particles by mixing (I) the fat emulsion with (II) (a) a pharmaceutical substance composition containing a pharmaceutical substance and a solvent or (b) a pharmaceutical substance composition containing a pharmaceutical substance and an excipient, and to a method of preparation of the pharmaceutical substance-containing fat emulsion.

BACKGROUND OF THE ART

Fat emulsion is a kind of emulsion having very fine particles of fat homogeneously dispersed in water. Especially, an intravenous fat emulsion has been developed for supplying calories to the patients who cannot take them orally and is now commercially available [cf. "the fundamentals and preparation of high-calorie transfusion solution": second press; p. 74–81, (1981); Sigehiko Shimada, YAKUJI NIPPO (Japan)]. Usually, fat emulsion means such intravenous emulsions.

This type of fat emulsion is normally prepared by heating the fat component such as soybean, cotton seed or safflower oil along with an emulsifier such as yolk phospholipid, lecithin or soybean lecithin, and other additives, roughly emulsifying them together with a needed amount of water by means of a homomixer, then finely emulsifying using a jet-type high-pressure homogenizer, and sterilizing with high-pressure steam.

The fat emulsion thus prepared is a homogeneous dispersion of oil-drop particles (of less than 1 micrometer average particle size) coated with an emulsifier on their surface in water. The oil-drop particles coated with an emulsifier on their surface is defined as "fat emulsion particles" here.

In recent years, a variety of trials have been made to develop more reasonable pharmacotherapy with increased efficacy and safety of medicinal substances by controlling the release of the substance from the preparation, preventing the substance from being inactivated in vivo, controlling the distribution of the substance in the living body, or prolonging the retention at the affected part. One of these trials is to develop a satisfactory carrier in which the pharmaceutical substance in the preparation is embedded. In this method, the behavior or efficacy of the pharmaceutical substance largely depend on the absorption, distribution, metabolism, and excretion of the carrier in vivo, differing from a usual preparation in which the pharmaceutical substance is released from the preparation, absorbed, distributed, metabolized and excreted alone in vivo.

The meaning of "a pharmaceutical substance is embedded in a carrier" is defined as follows:

A part or all of the molecules of the pharmaceutical substance constituting the preparation along with the carrier and others such as an excipinet are individually included in the carrier partially or entirely in their molecular bodies.

One of the examples of the entire part of one molecule of the pharmaceutical substance embedded in the carrier is the case in which the pharmaceutical substance is dissolved in the carrier, while an example of one molecule partially included is the case where a part of the molecule exists in the carrier and the rest is exposed to the outside.

Liposome of doubled lipid membrane has been known as such a carrier for a pharmaceutical substance.

Recently, however, trials of utilizing the above-stated fat emulsion particles as a carrier for embedding the pharmaceutical substance have been reported. They describe that the pharmaceutical substance-containing fat emulsion prepared by emulsifying the pharmaceutical substance along with fat and emulsifier prolonged the half-life in vivo of the substance compared with the case where the substance was given without the fat emulsion, and transferred the substance to the target site with selectivity increased.

As examples, are cited a steroid-fat emulsion [Japanese Patent, Laid-open No. 57-16,818 (1982)], a biphenylpropionic acid derivative-fat emulsion [Japanese Patent, Laid-open No. 60-16,923 (1985)] and a prostaglandin $E_1$-fat emulsion [Japanese Patent, Laid-open No. 58-222,014 (1983)]. The reason why the behavior in vivo of the pharmaceutical substance-containing fat emulsion differs from that of a preparation without the fat emulsion (such as a solution solubilized using a surface active agent) is thought that the pharmaceutical substance is embedded in the fat emulsion particles.

The process for preparation of such a pharmaceutical substance-containing fat emulsion is almost the same as that for preparation of the above-stated fat emulsion. In other words, a pharmaceutical substance to be embedded is dissolved in a specific amount of the oil component, mixed with an emulsifier and other additives, heated, then roughly emulsified along with a needed amount of water using a homomixer, finely emulsified into fine particles of less than 1 micrometer average particle size using a jet-type high-pressure homogenizer, and sterilized with high-pressure steam, after sealed in vessels.

The pharmaceutical substance-containing fat emulsion which is prepared by this method is very useful in medicinal therapy, but has several defects.

The first thing is that the pharmaceutical substance-containing fat emulsion cannot be stored for a long period of time, in case that the pharmaceutical substance is unstable in the fat emulsion. A countermeasure against the defect is, for example, to remove the components which makes the pharmaceutical substance unstable or to add an additive which stabilizes the substance. A former example is a prostaglandin fat emulsion which is stabilized by removing phosphatidyl ethanolamine from the phospholipid [Japanese Patent, Laid-open No. 60-149,524 (1985)]. This method is not, however, the universal one which can stabilize a number of medicines, because the main factors for stabilization are different depending on individual medicinal substances. Therefore, such a pharmaceutical preparation has been desired, as the pharmaceutical substance unstable can be applied in the stabilized form where the substance is embedded in the fat emulsion particles.

The second matter is that there are some pharmaceutical substance-containing fat emulsions which cannot be prepared by the above-stated method. For example, a jet-type high-pressure homogenizer is used in the method, and medicinal substances which explode by a shock cannot be made into the corresponding pharmaceutical substance-containing fat emulsions. Additionally, injection preparations require the high-pressure steam sterilization, but thermally sensible or volatile medicinal substances decompose or dissipate during the steam sterilization. In other words, the medicinal substances which is sensible to heat and highly volatile cannot be made into said pharmaceutical substance-containing fat emulsions.

Accordingly, the development has been desired on the preparations which enable the medicinal substances unstable to heat, shock or the like or highly volatile, to be applied by embedding them into the fat emulsion particles.

The present inventors have made intense investigation on the methods for preparing pharmaceutical substance-containing fat emulsions by mixing a fat emulsion with a pharmaceutical substance composition. Since the fat emulsion is a dispersion of oil or oil particles covered with a surface active agent on their surfaces, the inventors have thought that the pharmaceutical substance is taken into the fat emulsion particles according to the distribution coefficient between water and soybean oil, when the pharmaceutical substance composition is mixed with the oil emulsion.

If a pharmaceutical substance-containing fat emulsion can be prepared by mixing a pharmaceutical substance composition with a fat emulsion, the composition can avoid from the processes of the emulsification by means of a high-pressure jet type homogenizer and/or the sterilization with high-pressure steam. Additionally, if such a kit is provided, as a pharmaceutical substance-containing fat emulsion can be prepared by mixing the pharmaceutical substance composition with the fat emulsion, immediately before the preparation is applied, the stability of the pharmaceutical substance in the fat emulsion offers no longer problems.

Following prior arts have been known on the methods for preparation of such pharmaceutical substance-containing fat emulsions:

Fortner et al. described a method of mixing an anhydrous alcohol solution of an insoluble nitrosourea carcinostatic agent with a fat emulsion to prepare a fat emulsion containing the carcinostatic agent (cf. C. L. Fortner et al., Am. J. Hosp. Pharm. (1975) 32, 582–584).

El-Sayed et al disclosed a method for preparation of a fat emulsion containing a water-insoluble carbamic acid derivative, a carcinostatic agent, by dissolving the agent in a dimethylacetamide-cremophor ® mixture, and mixing the solution with a fat emulsion(cf. A. A. Fl-Sayed et al., International Journal of Pharmaceutics, 13, (1983), 303–312).

It has been found, however, by the present inventors, that, when an anhydrous alcohol or a dimethylacetamide-cremophor ® mixture is mixed with a fat emulsion in order to prepare a fat emulsion containing a sufficiently needed amount of a pharmaceutical substance for treatment, bubbles are formed in the emulsion, and the use of such pharmaceutical substance-containing fat emulsion as an injection is not undesirable from a safety point of view.

Consequently, it has been desired that a pharmaceutical substance-containing fat emulsion can be prepared, as the fat emulsion is kept stable, and solvents safe for medicinal substances will be found.

DISCLOSURE OF THE INVENTION

The present inventors have made intense studies on pharmaceutical substance compositions which exerts no adverse effect on the stability of the fat emulsion, and attained the present invention by finding following facts:

When a pharmaceutical substance composition which contains a pharmaceutical substance and at least one solvent selected from (1) water, (2) liquid polyalkylene glycols, (3) liquid trialkylamines, and (4) liquid polyhydric alcohols is mixed with a fat emulsion, the pharmaceutical substance is rapidly transferred and embedded into the fat emulsion particles, and the resultant pharmaceutical substance-containing fat emulsion can include a sufficiently needed amount of the pharmaceutical substance for treatment.

Further, the present inventors have found that, when a pharmaceutical substance composition containing a pharmaceutical substance as well as saccharides and/or amino acids as an excipient for the substance is mixed with a fat emulsion, the pharmaceutical substance is rapidly transferred and embedded into the fat emulsion particles to give a fat emulsion containing the pharmaceutical substance in a sufficient and necessary amount for treatment, and the excipient can also be added to the fat emulsion without any adverse effect on its stability.

Previously, "the embedment of a pharmaceutical substance into the carrier" was defined, and "a pharmaceutical substance is embedded in fat emulsion particles" has the same meaning as the previous definition except that the carrier is substituted with fat emulsion particles. In more detail, the fat emulsion particles are oil-drop particles which are covered with an emulsifier on their surfaces, and the existence of the whole part of one molecule of the pharmaceutical substance in a fat emulsion particle means that the whole molecule of the pharmaceutical substance dissolves or disperses in only the emulsifier part of the oil particles, in only the oil drop, or in both the emulsifier part and the oil drop.

In the meantime, the partial existence of one molecule of the pharmaceutical substance in the fat emulsion particle shows that a part of one molecule of the pharmaceutical substance distributes in only the oil particle, or in only the emulsifier part or in both the oil particle and the emulsifier part and the rest is outside the fat emulsion particle, in other word, exposed in the water phase.

A pharmaceutical substance which is stable in a conventional preparation process was used to compare a pharmaceutical substance-containing fat emulsion prepared by mixing the above-stated pharmaceutical substance composition with a fat emulsion with another pharmaceutical substance-containing fat emulsion prepared conventionally by dissolving the pharmaceutical substance in the oil and emulsifying the solution by the conventional method and their stability was found to be almost equal.

Thus, when a pharmaceutical substance-containing fat emulsion is prepared by mixing, immediately before the emulsion is applied, a pharmaceutical substance composition with a fat emulsion, a pharmaceutical substance which is unstable in the emulsion and cannot be used in the form of a pharmaceutical substance-containing fat emulsion by the conventional method becomes possible to be used in the form of a fat emulsion. Additionally, the pharmaceutical substance is not subjected to the processes with a jet type high-pressure homogenizer or with a high-pressure steam sterilizer, and pharmaceutical substances which are sensible to heat, shocks or highly volatile also can be prepared into a pharmaceutical substance-containing fat emulsion.

Moreover, the fat emulsion preparations produced by the process according to the present invention can be used as a preparation of excellent drug efficacy with reduced side effects, as in the conventional fat emulsions, showing a prolonged half life and increased selectivity to the target site.

Thus, the present invention is an extemporaneous type kit of pharmaceutical substance-containing fat emulsion, which is composed of (1) a fat emulsion, and
(2)
(a) a pharmaceutical substance composition containing a pharmaceutical substance and at least one solvent selected from water, liquid polyethylene glycols, liquid alkylethanolamines and liquid polyhydric alcohol, or
(b) a pharmaceutical substance composition containing a pharmaceutical substance and a saccharide and/or an amino acid as an excipient, and a method for preparation of a pharmaceutical substance-containing fat emulsion by mixing (1) a fat emulsion with
(2)
(a) a pharmaceutical substance composition containing a pharmaceutical substance and at least one solvent selected from water, liquid polyalkylene glycols, liquid alkylethanolamines and liquid polyhydric alcohols, or
(b) a pharmaceutical substance composition containing a pharmaceutical substance and a saccharide and/or an amino acids as an excipient, to embed the pharmaceutical substance into particles of the fat emulsion.

THE BEST EMBODIMENT OF THE INVENTION

The fat emulsion which constitutes the present invention is composed of (a) 0.1 to 50 w/v % of an oil component, (b) 1-50 parts, preferably 5-30 parts of an emulsifier, based on 100 parts of the oil component, and (c) a needed amount of water. Further, when needed, an emulsifying auxiliary, a stabilizer, an isotonicity, an antioxidant, a pH regulator also can be added.

The surface of the fat emulsion particles may be modified in order to increase the targeting efficiency toward the target site, strengthen the structure of the fat emulsion particles and inhibit the particles from being taken into the reticuloendothelial system.

The targeting efficiency toward the target site is increased by modifying with, for example, an immunoglobulin which specifically bonds to an antigen or an active fragment in an immunoglobulin or the incorporation into parenchyma cells of liver is increased with a fat emulsion particles having asialofetuin bonded to their surfaces. The incorporation into the reticuloendothelial system is inhibited by allowing glycofolin, a protein of erythrocyte membrane, to bond to the surface of the the fat emulsion particles. The structure of the fat emulsion particles is strengthened by modifying their surfaces with pullulan or amylopectin to which palmitic acid is bonded through the primary hydroxyl groups or with a cholesterol which is bonded to their particle surfaces through a crosslinking agent.

As an oil component for the fat emulsion according to the present invention, are cited soybean oil, cotton seed oil, safflower oil, corn oil, sesame oil, olive oil, triglycerides of medium-chain fatty acids, eicosapentanoic acid, and triacetin, but any other oil components also can be used without limitation, as long as they are usable for medicinal purposes. Especially, highly purified soybean oil (which is produced by subjecting normally purified soybean oil to further purification such as steam distillation [cf. H. J. Lips , J. Am. Oil Chemist, Soc., 27, 422–423 (1950)], and contains more than 99.9% of triglycerides, diglycerides and monoglycerides) is preferred.

As the emulsifier for the fat emulsion according to the present invention, are employed phospholipid, lecithin, hydrogenated lecithin, or nonionic surface active agents. But, any other emulsifiers also can be applied, as far as they are usable for medicinal purposes. Any phospholipid, lecithin or hydrogenated lecithin can be used regardless of their origins, and the substances originating from vegetable oil such as soybean oil or from animals such as yolk are employed. Phospholipid is preferably used in its purified form, and the purified product is prepared by a usual fractionation with organic solvents. In other words, for example, crude egg yolk 130 g is dissolved in a cooled n-hexane-acetone 200 ml : 100 ml mixture, then cooled acetone 1,170 ml is gradually added to the solution under stirring. The insoluble fraction is recovered by filtration, then dissolved again in a cooled mixture of 260 ml n-hexane and 130 ml acetone, then cooled acetone 1,170 ml is added under stirring, and the insoluble fraction is recovered by filtration. Finally, the solvent is distilled off, whereby the dried product 60 g is obtained. The product contains 70 -80% of phosphatidyl choline and 12-25% of phosphatidyl ethanolamine, additionally other phospholipids, phosphatidyl inositol, phosphatidyl serine and sphingomyelin [cf. D. J. Hanahan et al., J. Biol. Chem., 192, 623-628 (1950)]. Lecithin is an alias of phosphatidyl choline and obtained by subjecting a purified phospholipid to column chromatography, by chemical synthesis such as esterification of CDP choline with 1,2-diacylglycerol, or by enzymatic reactions such as acylation from Co A into lysolecithin. Many lecithins bear unsaturated fatty acids, and the unsaturated bonds are hydrogenated, for example, by catalytic reduction to give the hydrogenated lecithins resisting to oxidation.

The nonionic surface active agent is, for example, polyoxyalkylene copolymer, polyalkylene glycol, hydrogenated castor oil, polyoxyalkylene derivatives, or castor oil-polyoxyalkylene derivative, and polyoxyethylene-polyoxypropylene copolymer, hydrogenated castor oil-polyoxyalkylene alkyl ether or castor oil-polyoxyethylene alkyl ether of 2,000–20,000 molecular weight.

In case of a phospholipid as an emulsifier, an antioxidant is preferably added. Any antioxidant can be used, as long as it is usable as a medicinal component, and vitamin E is particularly suitable.

As an emulsification auxiliary for the fat emulsion according to the present invention, can be used a fatty acid of 6-22 carbon atoms, preferably 12-20 carbon atoms, or its salt, but any other auxiliary can be employed, as long as it can be added to drugs without limitation. Particularly, naturally occurring fatty acid is suitable. The preferable fatty acids are, for example, stearic acid, oleic acid, linolic acid, palmitic acid or linoleic acid.

The salts of the fatty acids are any physiologically acceptable ones, for example, alkali metal salts such as sodium or potassium salt or alkaline earth metal salts such as calcium salt.

The amount of the emulsification auxiliary added is usually 0.3 (w/v) % based on the fat emulsion.

As a stabilizer for the fat emulsion according to the present invention, are used cholesterol, phosphatidic acid, or polymeric substances, and any other stabilizers can be employed without limitation, as far as they can be added to drugs. Albumin, vinyl polymers and non-ionic surface active agents are preferably used as a polymeric substance.

Polyvinyl pyrrolidone or the like are cited as a vinyl polymer.

As a nonionic surface active agent, are used polyalkylene glycol (for example, polyethylene glycol of 1,000–10,000, preferably 4,000–6,000 average molecular weight), polyoxyalkylene copolymer (for example, polyoxyethylene-polyoxypropylene copolymer of 1,000–20,000, preferably 6,000–10,000 average molecular weight), hydrogenated castor oil-polyoxyalkylene derivative (for example, hydrogenated castor oil-polyoxyethylene-(40)-ether, -(20)-ether, -(100)-ether), castor oil-polyoxyalkylene derivative (for example, castor oil-polyoxyethylene-(20)-ether, -(40)-ether or -(100)-ether.

The amount of these stabilizers added are different from one another, for example, the cholesterol is less than 0.5 (w/v) %, preferably 0.1 (w/v) %, while the phosphatidic acid is less than 5 (w/v) %, preferably less than 1 (w/v) %.

As the pH controller for the fat emulsion according to the present invention, are used sodium hydroxide, sodium carbonate, sodium hydrogen carbonate or hydrochloric acid, but any other controller can be used, as long as they are usable as a drug.

The isotonicity used for the fat emulsion according to the present invention is, for example, glycerol or glucose.

The pharmaceutical substance composition constituting the present invention is composed of (a) a pharmaceutical substance and at least one solvent selected from water, liquid polyalkylene glycols, liquid alkylethanolamines, and liquid polyhydric alcohols or (b) a pharmaceutical substance and saccharides and/or amino acids as an excipient. Further, when needed, a stabilizer can be added to increase the stability of the pharmaceutical substance.

An example of water used as a solvent is distilled water for injection and it can contain an isotonicity, a pH controller or other additives. An example of water containing an isotonicity is physiological saline solution.

An example of the liquid polyalkylene glycols is polyethylene glycol of 800 or less average molecular weight such as polyethylene glycol 200, polyethylene glycol 300, polyethylene glycol 400, or polyethylene glycol 700.

An example of the liquid alkylethanolamines is diethanolamine or triethanolamine.

An example of liquid polyhydric alcohols is propylene glycol.

The saccharides are, for example, glucose, mannitol, inositol, xylitol or lactose.

The amino acids are, for example, glycine, alanine, arginine.

The stabilizer which can be added to the pharmaceutical substance composition is, for example, a substance to prevent the pharmaceutical substance from being oxidized such as ascorbic acid, EDTA, tocopherol, butyl-hydroxytoluene, butyl-hydroxy-anisole, propyl gallate, tetrahydroxyldimethyl, or a preservative such as phenol, sorbic acid, cresol, salicylic acid, propionic acid, methyl p-hydroxybenzoate.

Examples of the isotonicity and pH controller which can be added to the water as a solvent are the same as those which have been cited in the description of the fat emulsion.

The pharmaceutical substance used in the present invention are the following compounds, their derivative and salts, and the substances of high lipid solubility or oil soluble derivatives are preferably used:

As steroids, are cited dexamethasone, dexamethasone palmitate, dexamethasone stearate, dexamethasone myristate, hydrocortisone, hydrocortisone palmitate, hydrocortisone stearate, hydrocortisone myristate, prednisolone, prednisolone palimitate, prednisolone stearate, prednisolone myristate or progesterone.

As prostaglandins, are cited prostaglandin $A_1$, prostaglandin $E_1$, prostaglandin $E_2$, prostaglandin $F_1$, prostaglandin $F_{2\alpha}$, prostaglandin $I_2$ and their derivatives such as 9(0)-methano-$\Delta^{6(9\alpha)}$-prostaglandin $I_1$ (isocarbacylin), 9(0)-methano-$\Delta^{6(9\alpha)}$-prostaglandin $I_1$ methyl ester, 20-methyl-9(0)-methano-$\Delta^{6(9\alpha)}$-prostaglandin $I_1$, 6-oxo-prostaglandin $E_1$, 15-methyl-prostaglandin $E_2$, 7-thia-prostaglandin $E_1$ methyl ester, 17,20-dimethyl-7-thia-prostaglandin $E_1$ methyl ester, 18,18,19,19-tetradehydro-16-methyl-9(0)-methano-$\Delta^{6(9\alpha)}$-prostaglandin $I_1$, 18,18,19,19-tetrahydro-16, 20-dimethyl-9(0)-methano-$\Delta^{6(9\alpha)}$-prostaglandin $I_1$.

As fat-soluble vitamins, are cited vitamin $A_1$, vitamin $A_2$, vitamin $A_3$, vitamin $A_1$ palmitate, vitamin $D_1$, vitamin $D_2$, vitamin $D_3$, vitamin $D_4$, $\alpha$-tocopherol, $\beta$-tocopherol, $\gamma$-tocopherol, $\delta$-tocopherol, vitamin $K_1$, vitamin $K_2$, vitamin $K_3$, vitamin $K_4$, vitamin $K_5$, vitamin $K_6$ and their derivatives.

Particularly, as derivatives of vitamin $D_3$, are cited activated vitamin $D_3$, for example, active form of vitamin $D_3$ bearing a hydroxyl group in the 1$\alpha$-position, such as 1$\alpha$-hydroxycholecaliciferol (1$\alpha$-OH-$D_3$), 1$\alpha$, 25-dihydroxy-chole-calciferol (1$\alpha$, 25-(OH)$_2$$D_3$), 1$\alpha$, 24-dihydroxy-chole-calciferol (1$\alpha$, 24-(OH)$_2$$D_3$), 1$\alpha$, 24,25-trihydroxy-chole-calciferol (1$\alpha$, 24,25-(OH)$_3$$D_3$), 1$\alpha$-hydroxy-24-oxo-chole-calciferol, 1$\alpha$, 25-dihydroxy-24-oxo-cholecalciferol, 1$\alpha$, 25-dihydroxy-cholecalciferol-26,25-lactone, 1$\alpha$, 25-dihydroxy-cholecalciferol-26,23-peroxylactone, 26,26,26,27,27,27-hexafluoro-1$\alpha$, 25-dihydroxy-cholecalciferol, or active form of vitamin $D_3$ which does not bear a hydroxyl group in the 1$\alpha$-position such as 25-hydroxycholecalciferol (25-OH-$D_3$), 24-oxocholecalciferol, 24,25-dihydroxycholecalciferol (24,25-(OH)$_2$$D_3$), 25-hydroxy-24-oxo-cholecalciferol, 25-hydroxycholecalciferol-26,23-lactone, or 25-hydroxycholecalciferol-26,23-peroxylactone.

As an anti-inflammatory, are cited, for example, ibuprofen, flufenamic acid, ketoprofen, indomethacin, and their derivatives.

As an antiviral, are cited acyclovir, interferon, azidethymidine, and their derivatives.

As an antibiotic, are cited, selected from the drug acting against gram-positive and -negative bacteria, cephalosporins, penicillins, erythromycins, kitasamycin, chloramphenicols, tetracyclines, streptomycins, kanamycins, oleandomycins, colistin, gentamicin, dibekacin, ribostamycin, lincomycin, and their derivatives. The drugs acting on fungi and protozoas are amphotericin B and its derivatives.

As a carcinostatic agent, are cited hexamethylmelamine, daunorubicin, doxorubicin, daunomycin, futraful, 5-FU, bleomycin, methotrexate, actinomycin D, mitomycin C, chlorambucil and their derivatives.

As an antiulcerative, are cited cimetidine, gefarnate, and their derivatives.

As an antihistaminic, are cited, chlorpheniramine maleate, diphenhydramine hydrochloride, and derivatives from chlorpheniramine and diphenhydramine.

As a drug for arrhythmia, are cited propranolol, ajimaline, alprenolol and their derivatives.

As a cardiotonic, are cited digoxin, deslanoside, G-strophanthin, isopreterenol, etilefrine, dopamine, ubidecarenone, and their derivatives.

As a vasodilator, are cited oxyfedrine, carbocromen, dipyridamole, isosorbide nitrate, nitroglycerin and their derivatives.

As a fibrinolytic agent, are cited urokinase and its derivative.

As a cholagogue, are cited dehydrocholic acid and its derivatives.

As a physiologically active peptide, are cited insulin, calcitonin, glucagon, lipocortin, atrial sodium diuretic peptide, erythropoietin, renin, angiotensin, kalliklein, interleukin 1, interleukin 2, interleukin 3, interleukin 4, tumor necrosis factor, and their fat-soluble derivatives.

As a Ca antagonist, are cited nifedipine, nicardipine and their derivatives.

Particularly, prostaglandins, their oil-soluble derivatives, vitamin $D_3$ and its activated derivatives, nitroglycerin are suitably used.

The fat emulsion constituting the present invention is prepared by, for example, the following process:

An emulsifier, for example, phospholipid, and, when needed, aforementioned additives, for example, an emulsification auxiliary, a stabilizer, an antioxidant, and a pH controller are mixed with an oil component such as soybean oil, and they are dissolved by heating at 40°-75° C. to form a solution. The solution is combined with a needed amount of water and emulsified using a usual mixer such as a homomixer at 20°-80° C. to form a rough emulsion. The stabilizer and the isotonicity may be added at this stage.

Then, the rough emulsion is finely particulated at 20°-80° C. by means of a homogenizer (for example, a high-pressure jet type homogenizer such as Manthon-Goulin type homogenizer or ultrasonic wave type homogenizer) to form a homogenized fat emulsion of extremely fine particles. The average particle size of the emulsion is less than 1.0 micron and its storage stability is very good.

In case of a Manthon-Goulin homogenizer, the rough emulsion is homogenized by exposing it to the first stage of pressure ranging from 100 to 150 kg/cm² zero to two times, then the second stage of pressure from 400 to 700 kg/cm² 5 to 15 times.

The fat emulsion is sealed in a vessel and desirably sterilized with high-pressure steam.

As for the preparation of a fat emulsion including surface-modified oil particles, for example, a fat emulsion having an active fragment of an immunoglobulin bonded thereto is prepared as follows:

The active fragment of an immunoglobulin is linked to the fat emulsion particles by introducing a lipophilic substance into the fragment of the immunoglobulin and allowing the fragment to come into contact with a pharmaceutical substance-containing fat emulsion (called method 1 hereinafter) or by adding an lipophilic substance on the preparation of the fat emulsion, and bonding the fragment directly or through a crosslinking agent, after the emulsion is formed. In method 1, the lipophilic substance is suitably introduced into the fragment of immunoglobulin using phospholipid, glycolipid, or fatty acid as a substance. When phosphatidyl ethanolamine (PE) is used as a phospholipid, the fragment of immunoglobulin is allowed to react with N-4-(p-maleimide-phenol)butylphosphatidylethanolamine (p-MPB) resultant from the reaction of the lipid with succinimidyl-4-(p-maleimidephenol) butyrate (SMPB) [cf. J. Biol. Chem. 257, 286 (1982)]. In case of ganglioside, a kind of glycolipid, the lipid is oxidized with periodic acid, then allowed to react with the fragment [cf. Biochem. Biophys. Acta, 640, 66 (1981)]. Further, when palmitic acid is used as a fatty acid, palmitic acid ester of N-hydroxysuccin-imide is allowed to react with the fragment of an immunoglobulin [Biochem. Biophys. Acta, 689, 31, (1982)]. The complex between the immunoglobulin fragment and the lipophilic substance is bonded to the surface of the fat emulsion particles by allowing the aqueous solution or suspension of the complex to come into contact with the fat emulsion which has been prepared as stated above. This contact is carried out, for example, by treating 10 parts by weight of the fat emulsion with 0.01-10 parts by weight of the complex in the form of 0.1-10% aqueous solution or suspension. The contact temperature is usually 4°-37° C., the contact time is usually 30 minutes-24 hours, stirring or shaking is preferred. In method 2, for example, the PE-MPB is added, when the fat emulsion is emulsified, so that the complex becomes 0.01-10 w/v %, to effect the contact between the emulsion and the immunoglobulin fragment, thereby the fat emulsion having an immunoglobulin fragment bonded thereto is obtained. The contact is carried out, for example, by treating 10 parts by weight of the fat emulsion with 0.01-10 parts by weight of the fragment in the form of 0.1 -10% by weight aqueous solution usually at 4°-37° C. for 30 minutes to 24 hours, preferably under stirring or shaking.

The pharmaceutical substance composition containing medicinal substances and a solvent, one of the pharmaceutical substance compositions constituting the present invention, is prepared, for example, by the following method:

The pharmaceutical substance is dissolved in a solvent and the solution is sterilized by filtration. Then, the solution is enclosed in a vessel to provide a liquid pharmaceutical substance composition. The amount of such a liquid pharmaceutical substance composition depends upon the amount of the pharmaceutical substance needed and the kind of the solvent used. When no bubble formation by mixing with the fat emulsion, the stability of the fat emulsion, and the migration of the pharmaceutical substance are taken into considerarion, the amount of water, as a solvent, is set to not more than 100 parts by volume per 100 parts of the fat emulsion, while in case of a liquid poly-alkylene glycol, it is not more than 20 parts by volume, preferably not more than 10 parts by volume per 100 part of the fat emulsion.

Among the pharmaceutical substance compositions which constitute the present invention, the pharmaceutical substance composition containing a pharmaceutical substance and an excipient is preferred to have fine particle sizes and large surface areas, because it must be rapidly admixed to the fat emulsion. To be concrete, the composition is prepared by dissolving the components in distilled water for injection, sterilizing by filtration through a 0.2 micrometer membrane, pouring the filtrate into vessels and freeze-drying.

The amount of the pharmaceutical substance composition containing a pharmaceutical substance and an excipient varies with the quantity of the pharmaceutical substance needed, and is preferably less than 10 parts by weight per 100 parts by weight of the fat emulsion.

The extemporaneous kit of a pharmaceutical substance-containing fat emulsion is applied, for example, as follows:

When applied, the fat emulsion in an ampoule is poured into another ampoule containing the pharmaceutical substance composition and they are thoroughly mixed. The pouring operation can be sterilely conducted. The mixing here is usually achieved by shaking strongly by hand for at least 1 minute or by means of Voltex type shaker for at least 30 seconds at the maximum shaking intensity.

The resultant pharmaceutical substance-containing fat emulsion is preferably applied within a period of time, while the pharmaceutical substance is kept stable.

Further, the pharmaceutical substance-containing fat emulsion which has been prepared from the kit according to the present invention is used as an injection, desirably intravenous injection, but may be also given, after it is mixed with a transfusion solution such as isotonic sodium chloride solution or 5% glucose solution.

The present invention will be illustrated in more detail by the following examples, but the present invention is not limited thereto.

EXAMPLE 1

(1) The preparation of an extemporaneous kit a. Fat emulsion

A fat emulsion of the following formulation was prepared, poured into vials 2 ml each, and the vials were tightly stoppered with rubber caps, respectively.

| <Formulation of the fat emulsion> | |
|---|---|
| Purified soybean oil | 50.0 g |
| Purified yolk lecithin | 6.0 g |
| Glycerin for injection | 12.5 g |
| Distilled water for injection an appropriate amount | |
| Total | 500 ml | b. Indomethacin composition

Indomethacin was dissolved in polyethylene glycol 400 to form a solution of 10 mg/ml concentration, and the solution was sterilized by filtration through 0.2 micrometer membrane filter, poured into vials 0.1 ml each, and tightly stoppered with a rubber cap, respectively.

(2) Preparation of an indomethacin-containing fat emulsion

The kit prepared in (1) was used to take out the fat emulsion from vial (a) with a syringe, and inject the emulsion into the indomethacin composition in vial (b), then shaking the mixture thoroughly to provide an indomethacin-containing fat emulsion.

The indomethacin-containing fat emulsion was centrifuged with 120,000×g for 2 hours and separated into the oil phase and the aqueous phase. Then, the indomethacin in the oil phase was determined and found to be 54.0% based on the total weight in the preparation.

In the meantime, indomethacin was dissolved in soybean oil and emulsified by the conventional method, namely using yolk lecithin to form another indomethacin-containing fat emulsion having the same formulation as in (1) a. In this emulsion, 50.0% of the total indomethacin was found in the oil phase.

Thus, the mixing of the pharmaceutical substance composition with the fat emulsion also gave the substantially same pharmaceutical substance-containing fat emulsion as that prepared by the conventional method.

The indomethacin used in the kit according to the present invention was found to be stable for at least 24 hours in the fat emulsion.

EXAMPLE 2

(1) Preparation of extemporaneous kit a. Fat emulsion

A fat emulsion was prepared as in Example 1 to obtain a vial including 5 ml of the fat emulsion.

b. Liquid chlorambucil composition

Chlorambucil, a carcinostatic agent, is dissolved in propylene glycol in 10 mg/ml concentration, then the solution was sterilized by filtration through 0.2 micrometer membrane filter, and poured in vials 0.2 ml each and tightly stoppered with a rubber cap, respectively.

(2) Preparation of chlorambucil-containing fat emulsion

The fat emulsion was taken out of the vial (b) and poured into the vial (a) containing the chlorambucil composition, then they were thoroughly mixed for 1 minute to give a chlorambucil-containing fat emulsion.

As in Example 1, the chlorambucil in the oil phase was determined and found to be 65.0% based on the total weight in the composition.

In the meantime, another chlorambucil-containing fat emulsion of the same formulation as in Example 1 (1) a was prepared by the conventional process, namely by emulsifying soybean oil with yolk lecithin and found to contain 65.0% of chlorambucil in its oil phase.

Thus, almost the same pharmaceutical substance-containing fat emulsion as that prepared by the conventional method was obtained by mixing the pharmaceutical substance composition with the fat emulsion according to the present invention.

The chlorambucil in the kit according to the present invention was found to be stable in the fat emulsion for at least 72 hours.

Moreover, for comparison, a composition of chlorambucil dissolved in ethanol was used to prepare a chlorambucil-containing fat emulsion as in the above-stated method, and the formation of bubbles was observed in some fat emulsion, which is improper to be used as an injection. On the contrary, the kit with propylene glycol according to the present invention was found to be usable as an injection without change in the fat emulsion.

EXAMPLE 3

(1) Preparation of an extemporaneous kit a. Fat emulsion

Vials containing 2 ml of the fat emulsion were obtained as in Example 1.

b. 9(0)-methano-$\Delta^{6(9\alpha)}$-prostaglandin $I_1$ methyl ester composition 9(0)-methano-$\Delta^{6(9\alpha)}$-prostaglandin $I_1$ methyl ester was dissolved in triethanolamine in 40 micrograms/ml concentration, the solution was sterilized by filtration through a 0.2 micrometer membrane filter, then poured in vials 50 microliters each, and thightly stoppered with a rubber cap, respectively.

(2) Preparation of 9(0)-methano-$\Delta^{6(9\alpha)}$-prostaglandin $I_1$ methyl ester-containing fat emulsion The fat emulsion was taken out of the vial (a) and poured into the vial (b) containing the drug composition, and they were thoroughly mixed to give 9(0)-methano-$\Delta^{6(9\alpha)}$-prostaglandin $I_1$ methyl ester-containing fat emulsion.

As in Example 1, 9(0)-methano-$\Delta^{6(9\alpha)}$-prostaglandin $I_1$ methyl ester in the oil phase of the resultant fat emulsion was determined and 70% of the total drug was found in the oil phase.

Meanwhile, another 9(0)-methano-$\Delta^{6(9\alpha)}$-prostaglandin $I^1$ methyl ester-containing fat emulsion of the formulation in (1) a of Example 1 was prepared by the conventional process, namely by emulsifying the soybean oil with yolk lecithin was found to have 68.5% of the methyl ester in the oil phase.

For comparison, 9(0)-methano-$\Delta^{6(9\alpha)}$-prostaglandin $I_1$ methyl ester was dissolved in a N,N-dimethylacetamide-cremophor ® 1:1 mixture in 40 microagrams/ml concentration and the composition was used to prepare another 9(0)-methano-$\Delta^{6(9\alpha)}$-prostaglandin $I_1$ methyl ester-containing fat emulsion as in the above-stated manner. At this time, a considerable amount of bubbles were formed in the fat emulsion and the emulsion in some vials was found to be improper for an injection. On the contrary, no change was observed in the fat emulsion from the kit according to the present invention using triethanolamine as a solvent, thus the fat emulsion was usable as an injection.

EXAMPLE 4

(1) Preparation of extemporaneous kit a. Fat emulsion

A fat emulsion of the following formulation was prepared, poured in vials 5 ml each, then tightly stoppered with a rubber cap respectively, and sterilized with high-pressure steam at 121° C. for 20 minutes.

| <formulation of the fat emulsion> | |
|---|---|
| Purified soybean oil | 50.0 g |
| Purified yolk lecithin | 6.0 g |
| Glycerin for injection | 12.5 g |
| Distilled water for injection | an appropriate amount |
| Total | 250 ml | b. Liquid nitroglycerin composition

Nitroglycerin was dissolved in distilled water for injection in 0.5 mg/ml concentration, sterilized by filtration through 0.2 micrometer membrane filter, then poured in vials 5 ml each, and tightly stoppered with a rubber cap, respectively.

(2) Preparation of nitroglycerin-containing fat emulsion

The kit prepared in (1) was used to take out the nitroglycerin composition from the vial (b) using a syringe and inject it into the vial (a) containing the fat emulsion, then the mixture was thoroughly mixed for about 1 minute to provide a fat emulsion containing 2.5 mg of nitroglycerin.

In the meantime, for comparison with the extemporaneous kit, another fat emulsion containing 2.5 mg of nitroglycerin per 10 ml of the fat emulsion was prepared by dissolving nitroglycerin in soybean oil at a ratio of 2.5 mg the former to 1 g the latter and mixing it with a fat emulsion of the same formulation as in (1) a of Example 1, and the distribution of nitroglycerin was determined and the content of nitroglycerin in the oil phase was found to be at most 1 mg/10 ml fat emulsion. Nitroglycerin was thought to decomposed in the course of the process.

Thus, an extemporaneous kit has enabled a nitroglycerin-containing fat emulsion to maintain its nitroglycerin content without reduction in the course of the process, on the contrary to the conventional fat emulsion.

EXAMPLE 5

(1) Preparation of an extemporaneous kit a. Fat emulsion

Vials containing the fat emulsion 1 ml each were obtained as in Example 1.

b. A powdery $1\alpha$, $25$-$(OH)_2D_3$ composition

A powdery pharmaceutical composition containing $1\alpha$, $25$-$(OH)_2D_3$ was enclosed in vials, after it is prepared as follows:

$1\alpha$, $25$-$(OH)_2D_3$ 0.1 mg was dissolved in Japanese Pharmacopoeia ethanol 0.1 ml. The solution was added to a solution of 50 g of glycine in 1,000 ml of distilled water for injection, stirred, filtered with a membrane filter. The filtrate was poured into vials for freeze-drying 1 ml each. These vials were freeze-dried, replaced the air inside with a nitrogen gas, and tightly closed with sterilized rubber stoppers and aluminum caps respectively. The resultant $1\alpha$, $25$-$(OH)_2D_3$-containing composition was found to include 0.1 μg of $1\alpha$, $25$-$(OH)_2D_3$ and 50 mg of glycine, respectively.

(2) Preparation of $1\alpha$, $25$-$(OH)_2D_3$-containing fat emulsion

The fat emulsion was taken out a vial(a), and poured into the vial including the $1\alpha$, $25$-$(OH)_2D_3$ composition (b), and they are thoroughly mixed for 2–3 minutes. The ratio of the drug in the liquid phase to the total amount of the drug in the $1\alpha$, $25$-$(OH)_2D_3$ was almost the same as in the $1\alpha$, $25$-$(OH)_2D_3$ fat emulsion prepared according to the conventional method. The $1\alpha$, $25$-$(OH)_2D_3$ was found to be stable at least for 6 hours in the fat emulsion.

(3) The stability of $1\alpha$, $25$-$(OH)_2D_3$ in the extemporaneous kit of $1\alpha$, $25$-$(OH)_2D_3$-containing fat emulsion After stored at 10° C. for 18 months, the extemporaneous kit of $1\alpha$, $25$-$(OH)_2D_3$-containing fat emulsion prepared in (1) had almost the same content of the drug as in before storage.

In the meantime, the $1\alpha$, $25$-$(OH)_2D_3$-containing fat emulsion was stored at 10° C. for 18 months, and the content of $1\alpha$, $25$-$(OH)_2D_3$ was found to be 78% content compared with before storage.

Thus, the extemporaneous kit enables the preparation of $1\alpha$, $25$-$(OH)_2D_3$-containing fat emulsion free from reduction in the content of $1\alpha$, $25$-$(OH)_2D_3$, even after storage for a long period of time.

EXAMPLE 6

(1) Preparation of extemporaneous kit a. Fat emulsion

Vials containing fat emulsion 1 ml each were obtained in the same manner as in Example 1.

b. Powdery 1α, 24-(OH)$_2$D$_3$ composition

A powdery pharmaceutical composition containing 1α, 24-(OH)$_2$D$_3$ was enclosed in vials, after it was prepared as follows:

1α, 24-(OH)$_2$D$_3$, 1 mg was dissolved in Japanese Pharmacopoeia ethanol, 1 ml. The solution was added to a solution of 1 g of EDTA, 5 g of sodium ascorbate, and 50 g of mannitol in 1,000 ml of distilled water for injection, stirred, filtered with a membrane filter, and the filtrate is poured into vials for freeze-drying 1 ml each. These vials were subjected to freeze-drying, replaced the air inside with nitrogen gas, and tightly closed with sterilized rubber stoppers and aluminum caps respcetively. The resultant 1α, 24-(OH)$_2$D$_3$-containing composition was found to contain, every vial, 1 μg of 1α, 24-(OH)$_2$D$_3$, 1 mg of EDTA, 5 mg of sodium ascorbate and 50 mg of mannitol.

(2) Preparation of 1α, 24-(OH)$_2$D$_3$-containing fat emulsion

The kit prepared in (1) was used, the fat emulsion was taken out from the vial (a) with an injection syringe and poured into the vial (b) containing the 1α, 24-(OH)$_2$D$_3$ composition, then they were thoroughly mixed for about 2 minutes to prepare a 1α, 24-(OH)$_2$D$_3$-containing fat emulsion which contains 1 μg of the drug and is used as an injection.

Meanwhile, for comparison with the extemporaneous kit, 1α, 24-(OH)$_2$D$_3$, 10 μg was dissolved in soybean oil 1 g and converted into a 1α, 24-(OH)$_2$D$_3$-containing fat emulsion with the formulation in Example 1, (1) a according to the conventional method. The fat emulsion contained 1 μg of 1α, 24-(OH)$_2$D$_3$ per 1 ml.

Subsequently, in order to enable the fat emulsion which was prepared by the conventional method to be applied as an injection, the emulsion was poured in vials, 2 ml each, the vials were tightly stoppered with rubber caps, and sterilized with high-pressure steam at 121° C. for 20 minutes. Thus, the content of 1α, 24-(OH)$_2$D$_3$ reduced to 81% based on before sterilization.

Thus, the extemporaneous kit has facilitated the preparation of the 1α, 24-(OH)$_2$D$_3$-containing fat emulsion which can be used as an injection without reduction in 1α, 24-(OH)$_2$D$_3$ content at the sterilization step in the conventional method.

EXAMPLE 7

(1) Preparation of extemporaneous kit a. Preparation of an antibody-binding fat emulsion 1) Preparation of fat emulsion Purified soybean oil, 100 g and purified yolk phospholipid, 12 g were added, and solubilized at 65°–75° C. using a homomixer. Then, distilled water for injection and Japanese Pharmacopoeia glycerol 25 g were added to the solution until the total volume reached 800 ml. A Manthon-Goulin homogenizer was used to effect emulsification by allowing the mixture to pass through at 120 kg/cm$^2$ at the 1st time, then at 500 kg/cm$^2$ 10 times.

2) Preparation of Fab' fragment in immunoglobulin

The Fab' fragment of anti-T-lymphocyte specific antibody was prepared by the method according to Martin et al (J. Biol. Chem. 257, 286, (1982)). In other words, anti-T-lymphocyte specific antibody was digested with pepsin, treated with DTT (dithiothraitol) at 5.5 pH, and purified with Sephadex G25 to give Fab' fragment.

3) Preparation of N-4-(p-maleimidephenol)butylphosphatidylethanolamine (PE-MPB)

Yolk-originating phosphatidylethanolamine (PE) 1.5 g was dissolved in anhydrous methanol 100 ml containing 0.28 ml of triethylamine, and treated with succinimidyl-4-(p-maleimidephnol) butyrate (SMPB) in a nitrogen gas atmosphere at room temperature for 2 hours. After completion of the reaction, the reaction mixture was purified with a silicagel column (chloroform-methanol) to give PE-MPB.

4) Binding of PE-MPB with Fab' fragment

PE-MPB 1.2 ml was combined with 10 ml of 0.27 w/v % Fab' fragment aqueous solution (containing 20 mM citric acid, 35 mM disodium phosphate, 108 mM NaCl, and 1 mM EDTA at pH 6.0) to conduct the reaction with stirring at room temperature in a nitrogen gas atmosphere for 10 hours. The reaction mixture was purified with Sephadex G-25 to give PE-MPB-Fab' conjugated product.

5) Binding of the antibody with fat emulsion

The PE-MPB-Fab' conjugated product obtained in 4) (1.38 mg/ml), 2 ml was added to the fat emulsion obtained in 1), 8 ml to effect the reaction with stirring at room temperature in a nitrogen gas atmosphere for 16 hours thereby an anti-T-lymphocyte specific antibody-binding fat emulsion was obtained.

The antibody-binding fat emulsion is poured into vials 2 ml each, and tightly stoppered with rubber caps respectively.

b. Preparation of liquid dexamethasone palmitate composition

Dexamethasone was dissolved in propylene glycol in a concentration of 10 mg/ml, filtered with a 0.2 μm membrane filter to effect mechanical sterilization. The filtrate was poured into vials 0.1 ml each, then the vials were stoppered with rubber caps respectively.

(2) Preparation of dexamethasone palmitate-containing antibody-binding fat emulsion The antibody-binding fat emulsion was taken out of the vials prepared in (1) a. and poured into the vials containing the liquid dexamethasone palmitate composition obtained in (1) b., and they were thoroughly mixed. The dexamethasone palmitate-containing antibody-binding fat emulsion had the same ratio of the drug in the oil phase to the total drug as in the antibody-free dexamethasone-containing fat emulsion which was prepared by the conventional process.

EXAMPLE 8

(1) Preparation of extemporaneous kit a. Fat emulsion

A fat emulsion was prepared in the same manner as in Example 1 to obtain vials containing 1 ml of fat emulsion each.

b. Actinomycin D composition

Actinomycin D was dissolved in a distilled water for injection-propylene glycol 1:1 mixed solvent to form a solution of 2.5 mg/ml concentration. The solution was mechanically sterilized with 0.2 μm membrane filter, poured into vials 0.1 ml each, and stoppered with rubber caps respectively.

(2) Preparation of actinomycin D-containing fat emulsion

The fat emulsion was taken out of the vials (a), poured into the vials (b) containing actinomycin D, and they were thoroughly mixed for 1 minute.

In the actinomycin D-containing fat emulsion, 75.0% of the total actinomycin D was included in the oil phase.

In the meantime, actinomycin D was dissolved in soybean oil, and the solution was emulsified in the formulation as in Example 1 (1) a., in the conventional manner, namely using yolk lecithin. In the preparation, 73.0% of the total actinomycin D was included in the oil phase.

THE POSSIBILITY OF INDUSTRIAL APPLICATION

The present invention enables a pharmaceutical substance which has been desired to be given in the fat emulsion form in which it is embedded into the fat emulsion particles, but cannot be stored for a long period of time by conventional techniques, because they were unstable in the fat emulsion, to be administered in the fat emulsion form. Further, the present invention permits a pharmaceutical substance which cannot conventionally be embedded in the fat emulsion, because it is unstable to heat shock or the like or volatile, to be administered in the fat emulsion form in which the substance is embedded in the emulsion fat particles.

Accordingly, the development of pharmaceutical substances-containing fat emulsions which are very useful from a medicinal point of view, because they have very excellent drug efficacy with reduced side-effects has becomes possible and it is very significant.

We claim:

1. A medicinal kit which consists of:
    (1) a first container means containing a fat emulsion; and
    (2) a second container means containing a pharmaceutical substance; and either
        (a) at least one solvent selected from the group consisting of liquid polyalkylene glycols, liquid alkylethanolamines, and liquid polyhydric alcohols; or
        (b) at least one excipient selected from the group consisting of a saccharide and an amino acid,
    wherein the pharmaceutical substance is at least one member selected from the group consisting of steroids, carcinostatics, prostaglandins, fat-soluble vitamins, anti-inflammatories, caridiotonics, antiarrhythmics, vasodilators, and calcium antagonists whereby the contents of said first container means and of said second container means are mixed upon use to form a resulting composition.

2. The medicinal kit according to claim 1, wherein the fat emulsion is composed of:
    (a) 0.1–50 w/v % of an oil component;
    (b) 1–50 part by weight of an emulsifier per 100 parts by weight of the oil component; and
    (c) water.

3. The medicinal kit of claim 2, wherein the oil component is at least one member selected from the group consisting of soybean oil, cotton seed oil, safflower oil, corn oil, sesame oil, olive oil, medium chain fatty acid triglycerides, eicosapentanoic acid, and triacetin.

4. The medicinal kit of claim 2, wherein the emulsifier is at least one member selected from the group consisting of phospholipids, lecithin, hydrogenated lecithin, and nonionic surface active agents.

5. The medicinal kit according to claim 1 or claim 2, wherein the fat emulsion includes fat particles having an average particle size of 1 μm or less.

6. The medicinal kit according to claim 1, wherein the fat emulsion consists of fat emulsion particles whose surfaces are modified.

7. The medicinal kit according to claim 1, wherein the amount of component (2) is less than 10 parts by weight or volume per 100 parts by weight or volume of the fat emulsion.

8. The medicinal kit according to claim 1, wherein the liquid polyalkylene glycol is polyethylene glycol having an average molecular weight of 800 or less.

9. The medicinal kit according to claim 1, wherein the polyhydric alcohol is propylene glycol.

10. A method for preparation of a pharmaceutical composition comprising the step of admixing:
    (1) a fat emulsion, and
    (2) a composition comprising a pharmaceutical substance; and either
        (a) at least one solvent selected from the group consisting of liquid polyalkylene glycols, liquid alkylethanolamines and liquid polyhydric alcohols; or
        (b) at least one excipient selected from the group consisting of a saccharide and an amino acid, wherein the pharmaceutical substance is at least one member selected from the group consisting of steroids, carcinostatics, prostaglandins, fat-soluble vitamins, anti-inflammatories, caridiotonics, antiarrhythmics, vasodilators, and calcium antagonists.

* * * * *